United States Patent
Prelas et al.

(10) Patent No.: US 7,649,359 B2
(45) Date of Patent: Jan. 19, 2010

(54) ELECTROSTATIC THIN FILM CHEMICAL AND BIOLOGICAL SENSOR

(75) Inventors: Mark A. Prelas, Columbia, MO (US);
Tushar K. Ghosh, Columbia, MO (US);
Robert V. Tompson, Jr., Columbia, MO (US); Dabir Viswanath, Columbia, MO (US); Sudarshan K. Loyalka, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 217 days.

(21) Appl. No.: 11/639,405

(22) Filed: Dec. 13, 2006

(65) Prior Publication Data

US 2008/0007267 A1    Jan. 10, 2008

Related U.S. Application Data

(60) Provisional application No. 60/754,116, filed on Dec. 27, 2005.

(51) Int. Cl.
*G01N 27/00* (2006.01)
(52) U.S. Cl. ........................ 324/452; 324/71.1
(58) Field of Classification Search .............. 324/452, 324/71.1; 73/863; 204/164, 165
See application file for complete search history.

(56) References Cited

U.S. PATENT DOCUMENTS

| 5,766,934 | A | 6/1998 | Guiseppi-Elie | |
|---|---|---|---|---|
| 2004/0244889 | A1* | 12/2004 | Sailor et al. | 149/2 |
| 2005/0136548 | A1* | 6/2005 | McDevitt et al. | 436/180 |
| 2005/0282229 | A1 | 12/2005 | Su et al. | |
| 2007/0116607 | A1* | 5/2007 | Wang et al. | 422/83 |

OTHER PUBLICATIONS

B.M. Arora et al., "Deep-Level Transient Charge Spectroscopy of Sn Donors in $Al_xGa_{1-x}As$", *J. Appl. Phys.*, vol. 73, No. 4, Feb. 15, 1993, pp. 1802-1806.
D.V. Lang, "Deep-Level Transient Spectroscopy: A New Methodto Characterize Traps in Semiconductors", *Journal of Applied Physics*, vol. 45, No. 7, Jul. 1974, pp. 3023-3032.
V.I. Polyakov, A.I. Rukovishnikov, A.V. Khomich, B.L. Druz, D. Dania, A. Hayes, M.A. Prelas, R.V. Tompson, T.K. Ghosh, S.K, Loyalka, "Surface Phenomena of the Thin Diamond-Like Carbon Films," *Proceedings of the Materials Research Society*, vol. 555, 1999, pp. 345-350.

* cited by examiner

*Primary Examiner*—Vincent Q Nguyen
(74) *Attorney, Agent, or Firm*—Greer, Burns & Crain, Ltd.

(57) ABSTRACT

A chemical and biological agent sensor includes an electrostatic thin film supported by a substrate. The film includes an electrostatic charged surface to attract predetermined biological and chemical agents of interest. A charge collector associated with said electrostatic thin film collects charge associated with surface defects in the electrostatic film induced by the predetermined biological and chemical agents of interest. A preferred sensing system includes a charge based deep level transient spectroscopy system to read out charges from the film and match responses to data sets regarding the agents of interest. A method for sensing biological and chemical agents includes providing a thin sensing film having a predetermined electrostatic charge. The film is exposed to an environment suspected of containing the biological and chemical agents. Quantum surface effects on the film are measured. Biological and/or chemical agents can be detected, identified and quantified based on the measured quantum surface effects.

27 Claims, 3 Drawing Sheets

ELECTROSTATIC THIN FILM CHEMICAL AND BIOLOGICAL SENSOR

REFERENCE TO RELATED APPLICATION AND PRIORITY CLAIM

This application claims priority under 35 U.S.C. §119 from prior provisional application Ser. No. 60/754,116, entitled QUANTUM FINGERPRINT CHEMICAL AND BIOLOGICAL SENSOR filed Dec. 27, 2005.

STATEMENT OF GOVERNMENT INTEREST

This invention was made with government assistance from the Department of Energy Grant No ID NATO HITECH.LG 970587. The Government has certain rights in the invention.

FIELD OF THE INVENTION

A field of the invention is chemical and biological sensors. Sensors and methods of the invention can find use in many industries, including, for example, the defense, automotive, chemical processing, aerospace, electric/gas utilities, medical diagnostics/monitoring, environmental monitoring, and process control industries.

BACKGROUND OF THE INVENTION

Sensor development is a fertile field of investigation, having crucial importance in both economic prosperity and national security. For example, non-imaging sensors are used to monitor such parameters as temperature, acceleration, pressure, position, relative humidity, voltage and current, which are particularly helpful in industrial applications such as automobile engine control systems and flexible computer integrated manufacturing. Sensors and signal processing allow automated systems to interact with the external world, and are important components of vital systems in the fields of defense, aerospace, bioprocessing, human health care, manufacturing, pollution control, transportation and telecommunications.

Sensors also play an important role in analyte detection. Analyte detection can serve many purposes. The identification of analytes is useful in myriad applications across many industries. Reliable, efficient, inexpensive, and fast recognition of chemical and biological analytes is an important goal in many applications and industries.

One of the more recent concerns and applications for chemical and biological sensors relates to human safety. Detecting hazardous chemical and biological agents is useful in manufacturing facilities and health facilities, for example. The risk of chemical and biological terrorism provides a role for chemical and biological sensors, as well. Prominent biological agents for bioterrorism, threats of bioterrorism, and biological warfare, such as *Bacillus anthracis* spores, botulinum toxin, smallpox, and plague, are reasonably easy to prepare and disperse, and have the potential to inflict horrific injury and death upon a population.

Biological and chemical sensors must operate in difficult environments. A typical analyte detection environment can include many other agents that can make detection of the analyte(s) of interest difficult. Example agents that can thwart detection include various gaseous chemical compounds, microorganisms, and particulate matter. For example, a sensor for detecting chemical and bioterrorism agents can operate in an environment with hundreds of ambient chemicals, many microorganisms, and many other particles.

Also, it is useful for a signal sensor to detect multiple analytes and be able to provide a definite indication of both. However, many sensors are chemically prepared to attract a single type of analyte. In environments where there are multiple analytes of concern, multiple single analyte sensors are required.

Detection of biological agents in particular is also difficult owing to the relatively large size of most biological agents. For example, even one of the smallest biological agents, aflatoxin, weighs approximately 300 daltons (Da), whereas bacterial spores such as anthrax weigh approximately 667 million times more than aflatoxin. Biological agents include as many as 20 amino acids, and cells are complicated in that they include lipids in their membranes and other unique molecules as well.

In addition to hazardous material detection, drug control is another area that can benefit from a reliable chemical sensor. The Committee on Science of the $109^{th}$ Congress has urged research on detection, standardization, and remediation of methamphetamine (Meth). Their report indicates that Meth labs have grown from 218 in 1993 to 15,000 in 2004. This report brings out the urgent need for new Meth detection technologies with emphasis on field test kits and site detection. Testing of drugs and drug materials in a container is a major problem encountered by law enforcement officials. Limited amount of inspections of these containers are carried out manually and it is estimated that the U.S. now inspects 4 percent of the 6 million shipments that arrive at more than 100 ports, double the percentage before the September 11 attacks in 2001 [Edward J. Staples and Shekar Viswanathan, Paper read at the $7^{th}$ World Congress of Chemical Engineering, 10-14 Jul., 2005, Glasgow, Scotland]. Several government organizations such as the National Institute of Justice, Federal Bureau of Prisons, Department of Defense, Counter drug Technology Development Program Office, and others are working on developing sensitive sensors.

Existing sensors exhibit inherent drawbacks. One method for sensing biological agents includes traditional substrates, such as silicon or diamond-like carbon, for binding various enzymes, DNA, and proteins to a film, such as a diamond film. While this method is selective, it requires different enzymes for different purposes, and as such, each sensor must be designed for a specific agent. Moreover, this conventional method is an unduly slow process, is expensive, is limited to the detection of a single agent, and can only be used once. Additionally, conventional methods are often non-specific, and the equipment involved in conventional processes is often bulky or remote from the location to be tested.

Another drawback of conventional sensors and conventional sensing methods is that diffusion is relied upon to adhere a biological or chemical agent to a surface of the sensor. Thus, these conventional sensors and sensing methods are reliant upon a random process that results in a net loss of sensitivity by the sensor.

There are also several methods being investigated for biological agent detection. The most common method is the antibody-based detection and identification systems that can discriminate between biological agents on the three-dimensional structure of the component molecules of the agents. A second method is the Polymerase Chain Reaction (PCR) and gene probe based detection technique. The PCR uses the nucleic acid sequences of genes to differentiate the bioagent. Some biological molecules have unique ultraviolet light absorption properties. These molecules will then fluoresce at a specific wavelength that is detectable.

One approach tries to exploit these UV absorption and fluorescence properties. There are other approaches being investigated, including, for example, infrared backscatter for aerosol detection. This method can size a small particle but cannot distinguish it from a bio- or non-bio-aerosol. Manmade biological aerosols can have a unique shape and/or a unique size. It may be possible to develop methods to determine the size and shape of the aerosol. Biomolecules may have significant hydrophobicity and this may be used to detect bioagents. It may also be feasible to use a network of sensors to detect a two-dimensional pattern unique to a biological weapons attack. The primary problem which is shared by each of the above technologies is the time required for unambiguous detection. This is true whether or not the operational scenario is based on detect-to-warn or detect-to-treat objectives.

SUMMARY OF THE INVENTION

A chemical and biological agent sensor includes an electrostatic thin film supported by a substrate. The film includes an electrostatic charged surface to attract predetermined biological and chemical agents of interest. A charge collector associated with said electrostatic thin film collects charge associated with surface defects in the electrostatic film induced by the predetermined biological and chemical agents of interest. A preferred sensing system includes a charge based deep level transient spectroscopy system to read out charges from the film and match responses to data sets regarding the agents of interest. A method for sensing biological and chemical agents includes providing a thin film having a predetermined electrostatic charge. The film is exposed to an environment suspected of containing the biological and chemical agents. Quantum surface effects on the film are measured. Biological and/or chemical agents can be detected, identified and quantified based on the measured quantum surface effects.

DETAILED DESCRIPTION OF THE PREFERRED EMBODIMENTS

The invention provides a highly sensitive chemical and biological sensor capable of real time and simultaneous detection of multiple chemical and biological agents. A sensor of the invention includes a thin film possessing an electrostatic force at its surface that attracts chemical or biological agents to its surface. In preferred embodiments, a sensor includes a semiconductor or insulator substrate, and a charge collector for Q-DLTS measurements.

An example embodiment sensor of the invention includes thin sensing film possessing an electrostatic force is formed upon a substrate and a charge collector. Multiple charge collectors and films can be formed on a single substrate. Also, devices for heating of the film can be integrated on the substrate. Heat can be used to clean or renew the sensor's surface after a use.

In preferred embodiments, the thin film is a carbon based film with a surface termination that provides a negative electron affinity and positive electric charge. Other example embodiment sensors of the invention use thin semiconducting and insulating films, such as diamond-like films, silicon films, silicon carbide films, aluminum nitride films, sapphire films, gallium nitride films, and gallium phosphide films possessing an electrostatic force at the film surface.

A particularly preferred embodiment of the invention is a sensor including a thin diamond film terminated with fluorine. Other preferred embodiments are sensors including a thin diamond film terminated with oxygen or chlorine.

Sensors of the invention can be used to detect a wide variety of chemical and biological agents. Any chemical or biological molecule that can adhere to the film via the electrostatic force can be detected. Example biological agents include DNA, RNA, virus, cells, bacteria, organic molecules, etc.

A preferred interrogation method for a sensor film of the invention is charge-based Deep Level Transient Spectroscopy (Q-DLTS). With Q-DLTS sub-femtogram quantities of a chemical or biological agent can be measured. Sensor films in sensors of the invention do not rely upon diffusion or other imprecise or slow techniques for acquiring analyte. The electrostatic force on the surface of the film traps analytes, and can bind multiple different analytes of interest, particularly chemical and biological agents. The sensor film adheres biological and chemical agents even under difficult circumstances, such as an environment with hundreds of ambient chemicals, many microorganisms, and many other particles. The sensor is capable of distinguishing individual agents from a multicomponent mixture. The Q-DLTS interrogation can measure quantum states of the biological agent on the sensor's surface. Other interrogation methods include, for example indirect approaches which measure the local film resistance. These types of approaches integrate the current flow and do not provide specific information of the electron trap densities.

Embodiments of the invention provide a highly sensitive universal sensor and sensing method capable of simultaneous, real time detection of chemical and biological agents, ranging from cyanide to proteins. Embodiments of the invention include a readily portable, electrostatic solid-state film for measuring sub-femtogram quantities of a biological agent, and the sensor is capable of distinguishing individual agents from a multi-component mixture. The sensitivity inherent to the sensors of the invention, particularly when used with Q-DLTS interrogation enables detection of biological and chemical agents, and precursors thereto, before those agents are released. Moreover, embodiments of the invention may be readily analyzed, rendering them portable and secure in a variety of applications, including battlefield applications.

Preferred embodiment sensors and sensing methods will now be discussed with reference to the drawings. Drawings presented schematically will be understood by artisans with reference to the accompanying description here. Drawings are not to scale, and features may be exaggerated for purposes of illustration. Broader aspects of the invention will be recognized by artisans through the illustrated preferred embodiments.

Figure 1:
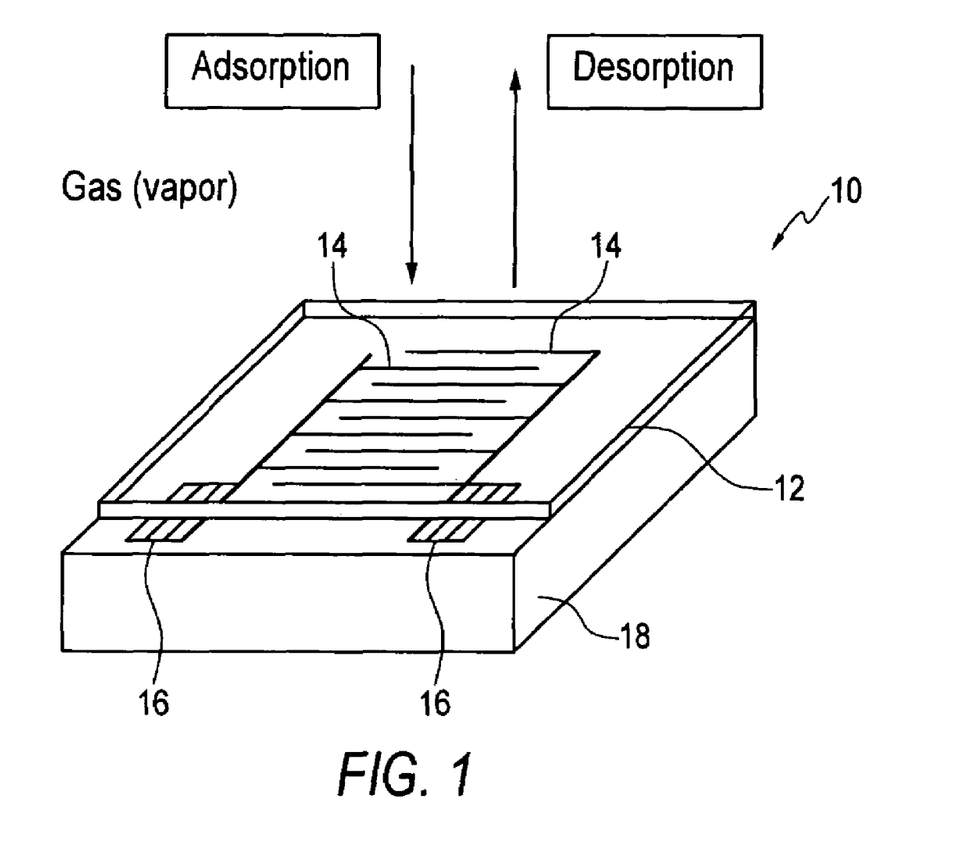
FIG. 1 is a schematic diagram illustrating an embodiment of a sensor of the invention and a method for sensing chemical and biological agents according to an embodiment of the invention.

FIG. 1 illustrates a preferred embodiment electrostatic thin chemical and biological sensor 10. The sensor includes an electrostatic thin film 12 that acts to adsorb biological and chemical agents. Any chemical or biological molecule that can adhere to the film via the electrostatic force can be detected. In preferred embodiments, a charge collector 14 for example a plurality of interdigitated conductive traces can heat the film 12. The charge collector 14, as illustrated in FIG. 1, terminates in contacts 16, but this represents an experimental embodiment. Other embodiments include sensor devices with multiple film areas and with integrated circuitry formed on a substrate 18 that supports the film. As an example, the charge collector 14 can form part of an integrated circuit that controls integration time cycles and includes operational amplifiers and circuitry to read out charges from one or more sensor films in cooperation with interrogation cycles used to detect chemical and biological agents that have been bound to the film 12 through electrostatic force. The charge collector 14 preferably has a structure and geometry to optimize charge collection from the film 12.

In preferred embodiments, the thin film 12 is a carbon based film with a surface termination that provides a negative electron affinity and positive electric charge. Other example embodiment sensors of the invention use thin semiconducting and insulating films, such as diamond-like films, silicon films, silicon carbide films, aluminum nitride films, sapphire films, gallium nitride films, and gallium phosphide films possessing an electrostatic force at the film surface.

A preferred embodiment diamond film 12 is highly sensitive and low noise. Indium provides good contact to diamond surfaces. A preferred collector is a multi-layer Ti/Pt/All collector. Another preferred collector is a multi-layer Ni/Cu/Au collector. In an experimental device that performed well, a collector included 100 nm Ti layer formed on a diamond-like film and topped with successive 60 nm Pt and 100 nm Au layers. Another example multi-layer is a 75 nm Ni, 40 nm Cu and 100 nm Au multi-layer.

The charged surface of the film 12 can be made via surface treatments. In preferred embodiments, the electrostatic charged film is achieved by treatment of the dangling carbon bonds (such as in a diamond film) on the film's surface to be terminated with fluorine. This type of surface treatment gives a diamond film surface a negative electron affinity. Thus, the surface of the film will have slight positive potential. This positive potential will attract bipolar molecules to the surface. Most chemical agents and biological agents are polar and thus will be attracted to the surface.

Once on the surface of the sensor material, each agent will create a unique surface defect structure. The presence and type of agents can be detected by an interrogation of the surface. A preferred interrogation method is the highly sensitive charge-based Deep Level Transient Spectroscopy (Q-DLTS) method, which measures surface defects on the film, Electrons are created by a series of voltage pulses. Some of the electrons are trapped. The electrons can be drained from the traps by temperature change or through a pulsed potential field.

The influence of adsorption of different agents on the density of surface states (i.e., electrically active trapping centers) and their spectral energy distribution is affected by the surface and bulk electronic properties. Q-DLTS has been used to study trapping centers in diamond films and has been reported to provide valuable information on the concentration of bulk and surface trapping centers, activation energy of the traps, re-distribution of the deep level densities in dependence on the film surface treatments and has been demonstrated as a sensor for various molecules. Q-DLTS is a preferred interrogation method that can provide information on the real energy distribution of the states in the film band gap. See, Polyakov et al., "Surface Phenomena of the Thin Diamond-Like Carbon Films", Proceedings of the Materials Research Society, Vol. 555, p. 345 (1999).

The response of an agent on the film 12 will be unique the specific agent can be identified as it will have a unique Q-DLTS spectrum. Q-LDTS is sensitive. The technique is especially powerful with preferred diamond films in that diamond is a low noise material due to it being a wide band-gap (5.49 eV). More generally, wider band-gap materials will provide a higher signal to noise ratio with the preferred Q-LDTS interrogation method than materials having lower band-gaps.

In the preferred Q-LDTS interrogation of the sensor 10, a current, voltage and time dependent spectrum is taken and can be used to determine the particular biological and chemical agents, which will have unique signatures that can be matched to a database developed in advance by testing agents of interest. Spectra of individual agents then can be used to identify the agent as well as determine the surface concentration of the electron traps, which is related to the concentration of agent on the surface. The spectrum obtained from the Q-DLTS interrogation is unique for each molecule bound to the electrostatic thin film 12. The spectrum characteristic is dependent only on the surface concentration of a type of molecule and temperature.

For a Q-DLTS interrogation an ASEC-3 system developed by Russian scientists and marketed through InOMTech Products, can be used. Sula Technologies, Oregon, also provides a suitable Q-DLTS system for interrogation. Q-LDTS systems allow the study of electrical properties (including parameters of the surface states and surface band bending) of insulating and semiconducting films.

The sensor and sensing methods of the invention are sensitive. The Q-DLTS interrogation uses transient signals that allow data to be pulled out of the noise level. This translates into high sensitivity. The sensitivity of the method is limited primarily by the number of manufacturing defects on the substrate material surface, the quality of the conductor interface with the sensor film, and the contact quality, all of which can have a minimum impact when a sensor of the invention is optimized through commercial fabrication techniques. Even laboratory sensors of the invention have demonstrated excellent sensitivity.

Sensors of the invention have been tested with various sensing materials (diamond-like films, polycrystalline diamond films and silicon carbide) on various molecules of interest (e.g., water, alcohol, lithium perchlorate, beryllium, TNT, marijuana, 2,5-Dimethoxy-4-methylamphetamine). The quality of the material has only been studied to some degree with polycrystalline diamond films where three grades (in order of quality: thermal grade, electronics grade and optical grade) were tested. The results indicated that the higher the quality of material the lower the noise level on the spectral measurements.

The sensor also has use as biological detector, for example to detect and identify virulent spores, e.g., *Bacillus stearothermophilus* spores, toxins, and other bioagents. The sensor film 12 can be doped to alter sensitivity.

For example, doped diamond films, because of their band structures, can have a greater sensitivity to certain bioagents. U.S. Pat. No. 5,597,762, Field-enhanced Diffusion using Optical Activation, is incorporated by reference herein, and discloses techniques for doping diamond films.

Forced diffusion achieves diamond doping. By using $LiClO_4$ as the impurity, n-type diamond films have been demonstrated successfully and n-type conduction in samples treated by this method was confirmed by other groups. A number of ions including Li, O, and Cl can be successfully diffused into diamond films. High-quality free standing "white" CVD diamond films, 230 mm thick, polished on both sides, with resistivity of 1014 Ohm-cm, have been demonstrated to obtain the n-type conductivity by forced diffusion with Li, O and Cl.

Sensors and sensing methods of the invention have many applications. An example application is as part of an integrated detection system for methamphetamine and related substances ammonia, acetone, and ether. Other systems of the invention test for chemicals such as phosphine, etc. Sensor systems of the invention can be implemented in a handheld and/or a desk-top versions, permitting field testing. Current wipe methods for field testing of meth, for example, are good in microgram [$10^{-4}$] levels, whereas a sensor of the invention should be able to measure picogram [$10^{-12}$] levels.

Additional Example Sensor Films.

| | |
|---|---|
| Texture/preferred crystallographic orientation | e.g.; (311), (100), (111), (110) |
| Grain size | e.g.; <1 µm, 10 µm, 100 µm |
| Surface finish (Ra) | e.g.; 3 µm, 0.3 µm, 100 Å |
| Surface treatment/surface termination | e.g.; H, O, Cl, F |
| Quality of bulk diamond (Raman FWHM) | e.g.; (<3, 5 cm$^{-1}$) |
| Metalization (surface contact grid) | e.g.; Ni, Ti/Pt/Au, Cr/Cu |
| Contact type | e.g.; ohmic, Schottky |

Performance is affected by the sensor materials. In particular, the bulk quality of the film material and the adsorption/desorption behavior of species on tetrahedrally bonded surface hydrogen, oxygen or other co-valently bonded elements impacts deep level transient response. Subtle differences in the behavior of bioagents under the effect of each of the variables above will affect the Q-DLTS response of the sensor, which is useful to differentiate between different bioagents and increase the sensitivity of the sensor.

Interrogation of a Sensor with Deep Level Transient Spectroscopy

When a molecule is deposited on a the surface of the sensor film 12, it will create a defect on that surface. The defect created on the surface can be determined by a preferred DLTS relaxation techniques, called Q-DLTS, which is based on the measurements of the transient process of the trapped charge after voltage or light. Voltage is applied to the surface using the collector. Light can be introduced, for example, by a flash lamp exposed to the surface. The voltage or light energizes the material and provides information about activation energy, capture cross-section, density of states and space distribution of active trapping centers (TC). This information provides a unique mapping of the molecule on the surface and as such provides a unique identifier of the agent of interest. In comparison with widely used capacitance-based DLTS, this charge-based method, due to measurements of the charge but not capacitance, gives one a possibility to investigate the structures which tend to be depleted at room or low temperatures and the high-frequency capacitance to be not dependent on the charge state of the interface and bulk traps (this is true, for example, for metal-insulator-metal structures or metal-insulator-semiconductor (MIS) structures in the case of pinning of the Fermi level).

In the Q-DLTS technique, cyclic bias pulses are applied to the sensor film 12 to change the charge state of the trapping centers. During the first part of a cycle the trapping centers are filled (before or after deposition) by applying a bias pulse to the sample. In the next part of the cycle, the trapped charge is emitted by changing the bias on the sample to zero. The charge emitted during the emission process can be collected by with integrator circuit, which can be part of a device integration on the substrate 18. The integrator circuit includes a high-speed operational amplifier with capacitance in the feedback loop.

The measured value of the Q-DLTS signal by this apparatus can be written as $\Delta Q = Q(t_1) - Q(t_2)$, where $t_1$ and $t_2$ are the times from the beginning of discharge. The charge $\Delta Q$ flowing through the circuit during the time period, $\Delta t = t_2 - t_1$, is measured as a function of parameters of the bias pulse, temperature, and rate window, $\tau_m = (t_2 - t_1)/\ln(t_2/t_1)$.

If it is assumed that the charge emission from the surface states after deposition varies exponentially with time, the measured value of the Q-DLTS signal can be written as $$\Delta Q = Q(t_1) - Q(t_2) = Q_0[\exp(-e_{p(n)}t_1) - \exp(-e_{p(n)}t_2)] \quad (1)$$

where, $Q_0 = \int Q_{00}(t)dt$, and $$e_{p(n)} = \sigma \Gamma_{p(n)} T^2 \exp(-E_a/kT) \quad (2)$$

is the hole (electron) emission rate from acceptor-like (or donor-like) traps, $\sigma$ is the capture cross-section, $\Gamma_{p(n)} = 2 \times 3^{1/2} (2\pi/h^2)^{3/2} k^2 m_{p(n)}^*$, T is the temperature, $E_a$ is the activation energy, h is the Planck constant, k is the Boltzmann constant, and $m_{p(n)}^*$ is the effective mass of the hole (electron).

1. The cycle of the preferred DLTS algorithm is different from that of Lang, "Deep-Level Transient Spectroscopy: A New Method to Characterize Traps in Semiconductors", Journal of Applied Physics, Vol. 45, No. 7 (1974). In Lang's algorithm, the time period $\Delta t$ (or rate window $\tau_m$) is kept fixed while the sample temperature is scanned to obtain the DLTS spectrum. The preferred alternative algorithm obtains the spectrum by scanning the rate window $\tau_m$ while keeping the temperature of the sample fixed. If we keep the ratio $t_2/t_1 = \alpha$ constant and vary $\tau_m = t_1(\alpha - 1)/\ln(\alpha)$, the functional dependence $\Delta Q(\tau_m)$ has a maximum which can be used to determine the trapping center parameters. Indeed, differentiating Eq. (1) with respect to $\tau_m$ we find that the maximum in $\Delta Q(\tau_m)$ occurs at the rate window equal to the emission rate of the traps, i.e. $\ln \alpha/(\alpha-1)t_1 = e_{p(n)}$. The emission rate of the traps can be found without recourse to temperature scanning, which takes considerable time. Furthermore, the trapping center concentration can be obtained from Q-DLTS spectra $\Delta Q(\tau_m)$ taken under isothermal conditions (at room temperature) as $N_t = 4\Delta Q_{max}/qA$, where
2. $\Delta Q_{max} = Q_0[\alpha^{1/(1-\alpha)} - \alpha^{\alpha/(1-\alpha)}]$
3. is the maximum value of the DLTS signal, q is the electron charge, and A is the contact area. In our measurements, if $\alpha$ is selected equal to 2, we will have $e_{p(n)} = \ln 2/t_1$ and $\Delta Q_{max} = Q_0/4$.
4. The activation energy $E_a$ and capture cross-section $\alpha$ are defined from the Arrhenius dependence of $\ln(\tau h d\, m^{-1}T^{-2})$ on $T^{-1}$ (as can be seen from Eq. 2) after measurements of Q-DLTS spectra at several temperatures.

Experiments

Experiments will now be discussed. Experiments have been conducted to verify the principles of the invention. The invention is not limited to the experimental devices and methods, as artisans will recognize that commercially fabricated devices and optimizations can be used to optimize sensing results using sensors and methods of the invention. Preferred fabrication techniques will also be discussed, and artisans will recognize various commercial fabrications based upon the description that are within the scope of the invention. Artisans will appreciate additional embodiments and broader aspects of such embodiments from the following discussions of experiments.

Figure 2:
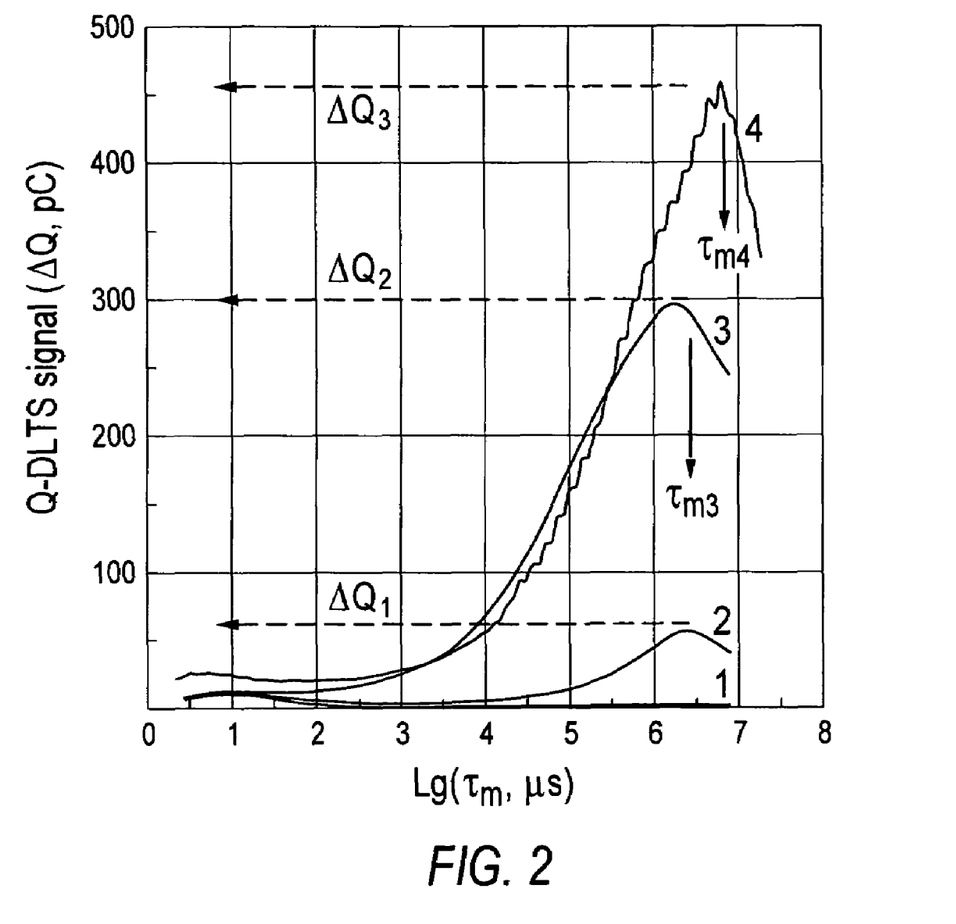
FIG. 2 is a graph of date from an experimental sensor according to FIG. 1 interrogated via Q-DLTS showing spectra for water vapor and alcohol.

A sensor consistent with the sensor 10 of FIG. 1 has been tested, for example, to demonstrate this ability to distinguish between water vapor and alcohol in an electrostatic diamond-like carbon film terminated with flourine. FIG. 2 show the spectra for water vapor and alcohol. FIG. 2 shows four signals labeled 1-4. Signal 1 is the film response after annealing at 440 K in air. Signal 2 is before annealing (room temperature). Signal 3 is film response when exposed to water vapor. Signal 4 is the film response in isopropyl alcohol vapor.

A typical sensor chip is made from a 1 cm×1 cm diamond film with a specific surface treatment and a conductor patterned on its detection face (although the size and surface treatment of the chip may vary depending upon detection needs). The sensor operates by collecting molecules on its surface. The molecules create surface defects which create a number of electron traps. The strength of the electron traps and the number of electron traps is a characteristic of the molecule that is on the surface. The characteristics of the electron traps can be measured using the highly sensitive Charge-based Deep Level Transient Spectroscopy (Q-DLTS). The response of each molecule is unique. The Q-DLTS spectrum of the sensor's surface defect density provides the means to determine the makeup of the molecules on the surface.

The key demonstration was that a unique change in surface potential was caused by the surface adsorbed molecules, and transient spectroscopy was able to differentiate these changes. This principle is extendable to more complex structures. An agent will be adsorbed on the surface based on thermodynamic principles. The agents will align themselves in a minimal energy configuration. This configuration will be unique and will change the local surface potential. This change in potential can be detected through the transient response of the system as measured by Q-DLTS.

Analysis of Data and Computations:

In the Q-DLTS technique the energy levels are repeatedly filled and emptied through use of voltage pulses. The responses of these pulses are monitored. The relaxation constants for single or multiple deep levels in a sensor, as induced by the substance under investigation, are then extracted from the recorded responses through data analysis. This extraction can be accomplished in several ways. In the simplest case, for a single deep level, one can reduce this extraction to a simple linear fit in several different ways. In the more general case, algorithms can be determined to extract strengths and relaxation constants for all induced deep levels that might be induced in the sensor by the substance. For example, the time response for a given choice of pulsing, can be represented by $$f[t] = \sum_{i=1}^{N} A_i e^{-t/\tau_i}$$

Fitting of this function to theoretically generated data sets (with random noise input) has been conducted. With the fitting, it was possible to extract the constants $A_i$ and $\tau_i$ for the simulated cases by using constrained minimization programs. These techniques can also be extended to the cases when there is a continuum of deep levels, in which case it is necessary to extract the form of the spectral function $g(\tau)$:

$$f[t] = \int_{\tau_1}^{\tau_2} g(\tau)\exp(-t/\tau)d\tau$$

Developing Data Sets and a Database

By testing, data sets can be developed for many chemical and biological agents of interested, and then when a sensor of the invention with an electrostatic thin film is exposed to an environment suspected of containing agents, the presence/absence of agents and their concentration can be determined after interrogation of the film. Data sets can be developed and stored for any and all agents that can bind to the electrostatic film in sensors of the invention. For example, data sets can be developed for agents of interest such as $C_{14}H_{26}O_4$, $CH_3(CH_2)_4COOCH_3$, $C_3H_9OP$, $C_3H_6N_6O_6$, $C_4H_8N_8O_8$. A sensor of the invention is exposed to each of the chemical or biological agents of interest. After the testing, a full range of deep level strengths, relaxation constants, and spectral functions as appropriate is extracted. This information is stored in a database, and can be used later to determined presence/absence, concentration information of chemical and biological agents of interest.

Data are always subject to some noise. Reverse Monte-Carlo methods and genetic algorithm can be used to make the inversion (extraction) process more robust. Such techniques will be especially useful for developing accurate data to detect multi-component agents of interest.

Example Fabrication of Electrostatic Diamond Sensor Film

A diamond chip is treated first with an acid to remove impurities from the surface. The dangling carbon bonds on the films can be terminated with flourine using a fluorine plasma, resulting in an electrostatic film.

Characterizing Concentration Responses

Figure 3:
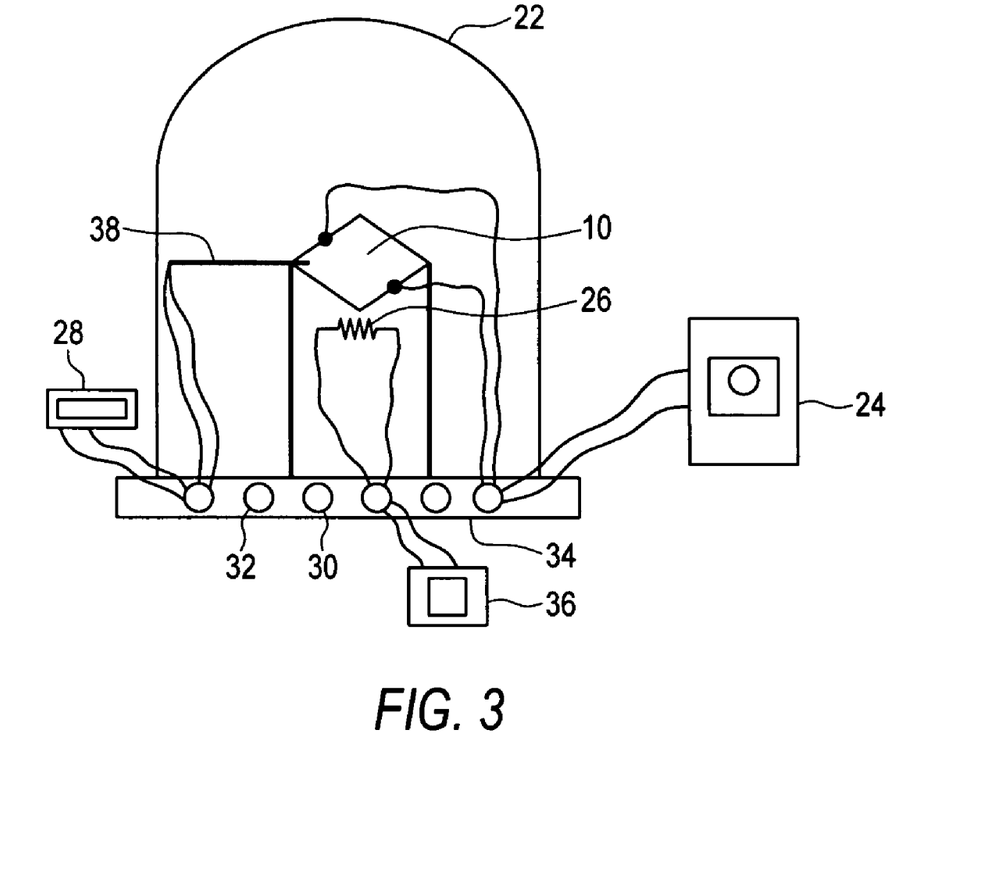
FIG. 3 shows an example embodiment system for calibrating and developing data sets for a sensor of the invention to determine and calibrate the response to chemical and biological agents.

FIG. 3 shows a system that can be used to develop data to characterize the level of response of a sensor 10 of the invention to the concentration of biological and chemical agents. An enclosure 22 supported by a base 34 encloses the sensor 10 for testing and provides a gas environment. A Q-DLTS system 24 monitors the sensor, which can be heated (such as for desoprtion) with a heater 26. A temperature read out 28 communicates with a thermocouple 38 to monitor temperature of the sensor 10. A gas inlet 30 and gas outlet 32 are used to control the environment within the enclosure, and a transformer/power supply 36 drives the heater 26 in a controlled fashion. The adsorption and desorption rate of the molecule on the sensor's surface, the sensor's temperature, the magnitude of the effect on the transient deep level response per molecule, the quality of the material, the contacts on the sensor, and the efficiency of the circuitry that plays an important role in the determination of density which can be experimentally determined and optimized. A schematic diagram of the system is given in FIG. 3. The system has already been designed. constructed, tested with a variety of chemicals.

Experimental Procedure/Determining Concentration Sensitivity

As seen in FIG. 3, a sensor chip 10 is mounted inside a stainless steel chamber 22. During testing, the chamber is evacuated to about $10^{-4}$ mmHg and a background reading on charge-current-time by a Q-DLTS system 24 that is connected to the contacts 16 is recorded. The chamber 22 is filled with dry-air to atmospheric pressure and again charge-current-time by Q-DLTS is obtained.

A predetermined amount of biological or chemical agent is then introduced in the chamber 22. The concentration of agent should be varied. Obtaining the lowest concentrations that the sensor can detect is achieved by successive dilution of the gas in the chamber. This can be achieved by pulling the vacuum (thus removing a portion of the gas from the chamber) and then again bringing it back to atmospheric pressure by introducing air. The concentration can be estimated from the gas law. The concentration can be lowered systematically to determine the lower level of detection.

In addition to pure component testing (of a single chemical or biological agent), a multi-component mixture can be prepared and tested in the chamber 22 to determine the response for individual component from its multi-component mixture. In developing a database for responses of various single components, experiment should be repeated a number of times to determine statistical validity of the data.

Sensor System Software and Database Integration

The software packages for commercially available DLTS systems can be used in the analysis of a sensor system of the invention, and the response database of sensor films in various embodiment sensor devices of the invention can be integrated into or used with the commercially available software. For example, the commercially available Sula DLTS use LabView, which is a robust user programmable control software package sold by National Instruments. Sula bases its control of its DLTS instrument on routines it has developed using the LabView protocol. A database of responses of the present sensor to chemical and biological agents can be developed as discussed above, and used with the Sula based control routine within LabView and streamlined for identification based on database matching routines implemented within the LabView protocol.

Additional Experimental Data

Current-voltage (I-V) characteristics for two sensors with different properties and film thicknesses. I-V characteristics (which usually are used for gas registration in solid state gas devices) did not noticeably change in the presence of gases or vapors. The capacitance-voltage characteristics taken from all conditions showed no voltage dependence of the capacitance. However, it was found that density of trapping centers $N_t$ obtained from Q-DLTS spectra strongly increases in the presence of water vapor (from $N_{t1}$ to $N_{t2}$) and in isopropyl alcohol vapor (from $N_{t1}$ to $N_{t3}$). The annealing of the sensor structures strongly decreases the density of trapping centers to $N_{t0}$.

The rates $N_{t2}/N_{t1}=\Delta Q_2/\Delta Q_1$ and $N_{t2}/N_{t0}=\Delta Q_2/\Delta Q_0$ were about 5 and 30 for water vapor and about 7 and 45 for isopropyl alcohol vapor, respectively. If one adsorbed molecule induces one trapping center, we are obtaining $N_{t2}-N_{t1} \approx 5 \times 10^{10}$ cm$^{-2}$—density of impurity water molecules, $N_{t3}-N_{t1} \times 8 \times 10^{10}$ cm$^{-2}$—density of impurity isopropyl alcohol molecules, and $N_{t1}-N_{t0} \approx 10^{10}$ cm$^{-2}$—density of the presented molecules on the sensor surface in air at room temperature. Depending on the size of the molecule, it is important to note that multiple trapping centers are created which further enhances the unique measurable response of the molecule. Sensitivity of the measurement system is $N_{tmin}=4\Delta Q_{min}/qA \approx 2.5 \times 10^3$ cm$^{-2}$. Furthermore, it was found that Q-DLTS spectra differ substantially between water and isopropyl alcohol adsorbents. In particular, $N_{t3}-N_{t2} \approx 3 \times 10^{10}$ cm$^{-2}$ and $\tau_{m4}-\tau_{m3} \approx 5$ sec.

Meth Detection

As an additional important agent to be tested, Methamphetamine response in a sensor of the invention was tested. The Meth was contained in a plastic bag and only a small portion of the bag was opened to let the vapor in the vicinity of the sensor. Several peaks of methamphetamine were detected and related to the different functional groups present in methamphetamine. Water (because of the one OH group) gave a single peak. The amount of meth was not even in nanograms as only the vapors that escaped from the plastic bag were sensed. The tests demonstrated that viable portable meth detection unit based upon a sensor of the invention can be constructed.

Active Toxic Substance Detection

Sensors of the invention, as mentioned have general applicability to chemical and biological agents. Some particular example toxic substances of interest include Exotoxins, which are toxic proteins excreted by bacteria. Another example is a virulent virus, e.g., smallpox, influenza. Another example is a virulent spore, e.g.: anthrax vaccine. Another example is a virulent bacterium.

Sensor Optimization

Polishing/Finishing:

The production of a uniform surface topography is desirable. For example, in the case of a diamond film sensor, a chemical vapor CVD diamond surface should be 1) be lithographically compatible, 2) promote consistent and reproducible surface-species "coverage" and adsorption/desorption behavior, and 3) prevent spurious electron emission from surface asperities (point, edge, facets) where unoccupied energy states may promote electron tunneling in the presence of the electric field during operation.

Finishing processes capable of producing smooth (<0.5 um-100 Å Ra) and flat CVD diamond substrates without introducing surface/sub-surface damage are preferred. The surface-specific roughness and "graded" columnar microstructure of as-deposited CVD diamond may require asymmetric (with respect to material removal) finishing processes to achieve the surface finish and flatness specifications. Such processes have been developed using fixed and slurry abrasive finishing techniques for CVD diamond and have produced rapid stock removal rates with high yields over 2"-4" diameter CVD diamond wafers. Surface rms roughnesses of less than 50 nm can be uniformly attained over 2-inch square substrates without evidence of microcracking, while maintaining the required flatness for subsequent lithography and metalization.

Surface-Chemical Terminations:

The electrical and photoelectrical properties of the CVD diamond surface significantly depend upon the terminal surface characteristics and associated surface Fermi level and interface band bending. Surface processing (thermal, chemical, plasma, metalization) has demonstrated a strong influence on band bending and electron affinity and would be expected to influence surface electrical properties. As electrically active trapping sites, surface defects can induce band bending and modify the Fermi level position. Therefore, surface processing can change the density of surface defects (surface states), change the surface barrier height, and control electron emission. In addition to Flourine, Hydrogen has been shown to induce negative electron affinity and oxygen and metal monolayers positive electron affinity on diamond surfaces. Wet-chemical and plasma-based techniques have been used to tailor the surface chemistry of CVD diamond and the desorption behavior of H—, O—, Cl and F-terminated CVD diamond surfaces has been examined and correlated with surface energy measurements. To implement specific embodiment sensors with different sensor films, the correlation of absorption/desorption behavior of the "species-of-interest" with the associated controlling surface defect(s) is determined in conjunction with characterization of the surface electrical response specific to sensor performance.

Metallization:

The metal-sensor film contact can exhibit rectifying Schottky or Ohmic characteristics (metal/semiconductor, $E_g$=5.5 eV). This I-V behavior depends upon the CVD diamond processing history. The surface termination chemistry and surface structural defects produce localized electron states, which add to the work function differences which exist between different contact metals and the sensor film material, e.g., diamond, and the contact processing history from metal deposition conditions to annealing treatments also affect behavior. Annealing has been shown to modify the metal/diamond contact resistance through the formation of an interfacial space-charge depletion region As-deposited metallization schemes using Ti, Mo, and Ta bonding layers to CVD diamond have demonstrated stable Schottky-like behavior, with nA-range leakage currents between −100V to +100V up to ~200 C. Isothermal and isochronal vacuum annealing of the metal/diamond couples showed an exponential decrease in contact resistance with annealing temperature for annealing times from 100 sec through 10000 seconds. They showed a constant, linear, contact resistance for a given temperature with increasing time, and following annealing the metal/diamond contacts exhibited Ohmic characteristics. The strong affinity of the diamond surface for H, O, Cl, and F species coupled with the influence of thermal processing on the metal/diamond interfacial density of states, surface barrier height, and hence contact electrical behavior, requires collective consideration of the operational environment of the sensor and the method for adsorption/desorption regulation of the sensor with respect to selectivity, sensitivity and calibration.

While various robust metallization schemes exist and are in manufacturing use, their compatibility with the present sensor methods and environments must be assessed and the response data sets developed as discussed above.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention.

What is claimed is:

1. A chemical and biological agent sensor (10), the sensor comprising:
    a substrate (18);
    an electrostatic thin film (12) supported by said substrate having an electrostatic charged surface to attract predetermined biological and chemical agents of interest; and
    a charge collector (14) associated with said electrostatic thin film to collect charge associated with surface defects in the electrostatic film induced by the predetermined biological and chemical agents of interest.

2. The sensor of claim 1, wherein said charge collector comprises interdigitated electrodes contacting said electrostatic thin film.

3. The sensor of claim 1, wherein said electrostatic film comprises a carbon based film having its carbon bonds terminated to form an electrostatic charged surface.

4. The sensor of claim 1, wherein said electrostatic film comprises a diamond film having surface carbon bonds terminated with an element to provide an electrostatic charge.

5. The sensor of claim 4, wherein said electrostatic film comprises a diamond film with fluorine terminated carbon bonds.

6. The sensor of claim 4, wherein said electrostatic film is a doped diamond film.

7. A chemical and biological sensor system, comprising:
    a sensor (10) according to claim 1;
    a charge based deep level transient spectroscopy (Q-DLTS) system (24) for analyzing charge response of the sensor, the spectroscopy system having access to data sets concerning the response spectra of the predetermined biological and chemical agents of interest.

8. The sensor of claim 1, wherein said electrostatic film comprises a carbon based film with fluorine terminated carbon bonds.

9. The sensor of claim 1, wherein said electrostatic film comprises a carbon based film with oxygen terminated carbon bonds.

10. The sensor of claim 1, wherein said electrostatic film comprises a doped diamond film.

11. The sensor of claim 1, wherein said electrostatic film comprises a semiconductor film with an electrostatic charge.

12. The sensor of claim 1, wherein said electrostatic film comprises an insulator film with an electrostatic charge.

13. The sensor of claim 1, wherein the charge collector comprises a multi-layer collector.

14. The sensor of claim 13, wherein the charge collector comprises one of a Ti/Pt/Al and Ni/Cu/Au collector.

15. The sensor of claim 1, wherein said film comprises a silicon film having its bonds terminated with another element to provide an attractant surface for chemical and biological agents.

16. The sensor of claim 15, wherein said film comprises a doped silicon film.

17. The sensor of claim 1, wherein said film comprises a silicon carbide film having surface bonds terminated with an element to provide an attractant surface for chemical and biological agents.

18. The sensor of claim 17, wherein said film is a doped silicon carbide film.

19. The sensor of claim 1, wherein said film comprises an aluminum nitride film possessing an electrostatic force at the film surface.

20. The sensor of claim 1, wherein said film comprises a sapphire film possessing an electrostatic force at the film surface.

21. The sensor of claim 1, wherein said film comprises a gallium nitride film possessing an electrostatic force at the film surface.

22. The sensor of claim 1, wherein said film comprises a gallium phosphide film possessing an electrostatic force at the film surface.

23. The sensor of claim 1, wherein said film comprises a crystalline film possessing an electrostatic force at the film surface.

24. The sensor of claim 1, wherein said electrostatic thin film comprises a crystalline film and said charge collector is patterned on an exposed face of said crystalline film.

25. The sensor of claim 1, wherein said electrostatic thin film comprises a polycrystalline film and said charge collector is patterned on an exposed face of said crystalline film.

26. A method for sensing biological and chemical agents, the method comprising:
    providing a sensing thin film having a predetermined electrostatic charge;
    exposing the sensing film to an environment suspected of containing the plurality of biological and chemical agents;
    measuring quantum surface effects on the sensing film;
    identifying the biological and chemical agents based on the measured quantum surface effects.

27. The method of claim 26, further comprising quantifying the biological and chemical agents based upon measured quantum surface effects.

* * * * *

UNITED STATES PATENT AND TRADEMARK OFFICE
CERTIFICATE OF CORRECTION

PATENT NO. : 7,649,359 B2
APPLICATION NO. : 11/639405
DATED : January 19, 2010
INVENTOR(S) : Prelas et al.

It is certified that error appears in the above-identified patent and that said Letters Patent is hereby corrected as shown below:

In the Specification:

Col. 8, lines 51-52

After "dependence of" please delete "$\ln(\tau hd\ m^{-1}T^{-2})$" and insert -- $\ln(\tau_m^{-1}T^{-2})$ -- in its place.

Signed and Sealed this

Seventeenth Day of August, 2010

David J. Kappos
*Director of the United States Patent and Trademark Office*